(12) United States Patent
Hu et al.

(10) Patent No.: US 11,992,843 B2
(45) Date of Patent: May 28, 2024

(54) DEVICE FOR DETECTING ANALYTE IN SAMPLE

(71) Applicant: ABBOTT RAPID DIAGNOSTICS INTERNATIONAL UNLIMITED COMPANY, Dublin (IE)

(72) Inventors: Haipeng Hu, Zhejiang (CN); Jianfeng Wang, Zhejiang (CN)

(73) Assignee: Abbott Rapid Diagnostics International Unlimited Company, Dublin (IE)

( * ) Notice: Subject to any disclaimer, the term of this patent is extended or adjusted under 35 U.S.C. 154(b) by 517 days.

(21) Appl. No.: 16/816,000

(22) Filed: Mar. 11, 2020

(65) Prior Publication Data
US 2020/0207523 A1 Jul. 2, 2020

Related U.S. Application Data

(63) Continuation of application No. 13/511,086, filed as application No. PCT/CN2010/001878 on Nov. 23, 2010, now abandoned.

(30) Foreign Application Priority Data

Nov. 23, 2009 (CN) .......................... 200910225108.X

(51) Int. Cl.
*B01L 3/00* (2006.01)
*A61B 10/00* (2006.01)
*B65D 41/04* (2006.01)

(52) U.S. Cl.
CPC .......... *B01L 3/508* (2013.01); *A61B 10/0096* (2013.01); *B65D 41/0471* (2013.01);
(Continued)

(58) Field of Classification Search
CPC ............ B65D 41/0471; B65D 2203/12; A61B 10/0096; A61B 10/0045; B01L 3/508;
(Continued)

(56) References Cited

U.S. PATENT DOCUMENTS

| 4,456,137 A | 6/1984 | Lyman |
| 4,934,547 A | 6/1990 | Mayes et al. |

(Continued)

FOREIGN PATENT DOCUMENTS

| CN | 1834622 A | 9/2006 |
| CN | 1879016 A | 12/2006 |

(Continued)

OTHER PUBLICATIONS

International Preliminary Report on Patentability received for PCT Patent Application No. PCT/CN2010/001878, dated Jun. 7, 2012, 8 pages.

(Continued)

*Primary Examiner* — Samuel P Siefke
(74) *Attorney, Agent, or Firm* — Edward J. Baba; Mandar A. Joshi; Bozicevic, Field & Francis LLP

(57) ABSTRACT

A device for detecting an analyte in a sample is provided, which comprises: a collecting chamber containing an opening for collecting a liquid sample; a detecting element for detecting an analyte in the liquid sample; and a lid for covering the opening of the collecting chamber. The device further comprises an indicating device thereon to indicate whether or not the lid covers at an appointed position. The operation of the device is very simple.

13 Claims, 7 Drawing Sheets

(52) U.S. Cl.
CPC ..... *A61B 10/0045* (2013.01); *B01L 2200/025* (2013.01); *B01L 2200/141* (2013.01); *B01L 2300/042* (2013.01); *B01L 2300/123* (2013.01); *B65D 2203/12* (2013.01); *Y10T 436/141111* (2015.01); *Y10T 436/142222* (2015.01); *Y10T 436/143333* (2015.01); *Y10T 436/144444* (2015.01); *Y10T 436/145555* (2015.01); *Y10T 436/146666* (2015.01); *Y10T 436/147777* (2015.01); *Y10T 436/173076* (2015.01); *Y10T 436/173845* (2015.01)

(58) Field of Classification Search
CPC ......... B01L 2200/025; B01L 2200/141; B01L 2300/042; B01L 2300/123; Y10T 436/141111; Y10T 436/142222; Y10T 436/143333; Y10T 436/144444; Y10T 436/145555; Y10T 436/146666; Y10T 436/147777; Y10T 436/173076; Y10T 436/173845

See application file for complete search history.

(56) References Cited

U.S. PATENT DOCUMENTS

| | | | |
|---|---|---|---|
| 4,976,923 A | 12/1990 | Lipsky et al. | |
| 5,429,804 A | 7/1995 | Sayles | |
| 5,586,671 A | 12/1996 | Thomas et al. | |
| 5,632,394 A | 5/1997 | Mecca et al. | |
| 6,277,646 B1 | 8/2001 | Guirguis et al. | |
| 6,726,879 B2 | 4/2004 | Ng et al. | |
| 7,270,959 B2 | 9/2007 | Hudak | |
| 7,300,633 B2 | 11/2007 | Hudak et al. | |
| 7,438,852 B2 | 10/2008 | Tung et al. | |
| 7,537,733 B2 | 5/2009 | Lappe et al. | |
| 7,560,272 B2 | 7/2009 | Ramsey et al. | |
| 2003/0027359 A1 | 2/2003 | Hudak et al. | |
| 2003/0059347 A1 | 3/2003 | Ostgaard et al. | |
| 2005/0074362 A1 | 4/2005 | Lappe et al. | |
| 2005/0106750 A1 | 5/2005 | Tung et al. | |
| 2005/0133396 A1 | 6/2005 | Daykin | |
| 2006/0186075 A1 | 8/2006 | Rainey et al. | |
| 2006/0280650 A1 | 12/2006 | Wong et al. | |
| 2007/0092402 A1 | 4/2007 | Wu et al. | |
| 2008/0230410 A1 | 9/2008 | Steven et al. | |
| 2013/0068649 A1 | 3/2013 | Chen | |

FOREIGN PATENT DOCUMENTS

| | | |
|---|---|---|
| CN | 201043969 Y | 4/2008 |
| CN | 101464457 A | 6/2009 |
| CN | 201302570 Y | 9/2009 |
| CN | 201572649 U | 9/2010 |
| JP | 2009-132464 A | 6/2009 |
| WO | 02/66335 A1 | 8/2002 |
| WO | 2004/103853 A1 | 12/2004 |
| WO | 2009/019097 A1 | 2/2009 |

OTHER PUBLICATIONS

International Search Report and Written Opinion received for PCT Patent Application No. PCT/CN2010/001878, dated Mar. 3, 2011, 13 pages.

Office Action received for European Patent Application No. 10831039.2, dated Aug. 14, 2018, 4 pages.

Office Action received for European Patent Application No. 10831039.2, dated Nov. 14, 2017, 4 pages.

Supplementary European Search Report and Written Opinion received for EP Patent Application No. 10831039.2, dated Jun. 1, 2016, 7 pages.

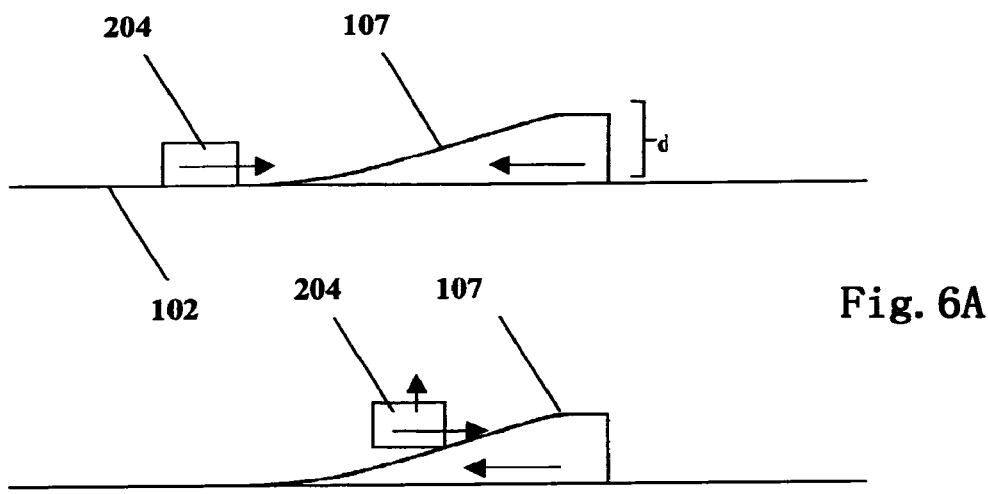
Fig. 6A
Fig. 6B
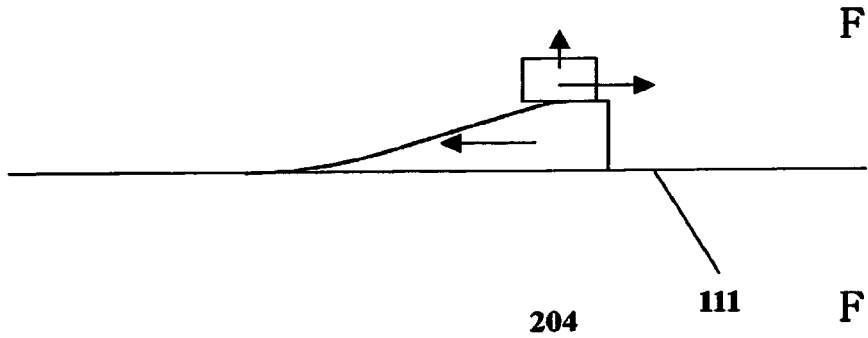
Fig. 6C
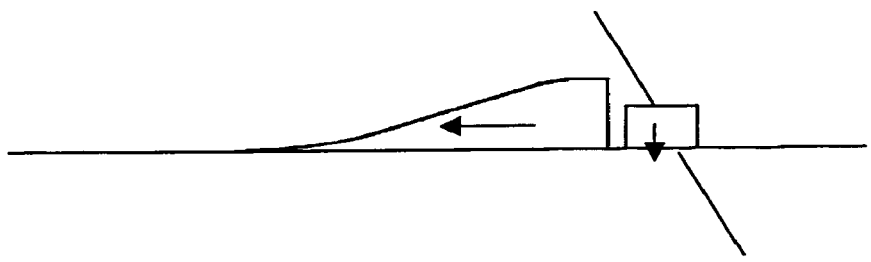
Fig. 6D

DEVICE FOR DETECTING ANALYTE IN SAMPLE

CROSS-REFERENCE TO RELATED APPLICATIONS

This application is a continuation of U.S. patent application Ser. No. 13/511,086 filed Sep. 14, 2012, now pending, which claims the benefit under 35 USC § 371 National Stage application of International Application No. PCT/CN2010/001878 filed Nov. 23, 2010, now expired, which claims the benefit under 35 USC § 119(a) to China Patent Application No. 200910225108.X filed Nov. 23, 2009. The disclosures of the prior applications are considered part of and are incorporated by reference in the disclosure of this application in their entireties.

BACKGROUND OF THE INVENTION

Field of the Invention

The present invention relates to a device for detecting whether or not an analyte exists in a liquid sample.

Background Information

In the field of medical care, detecting body fluid is a prevailing behavior. Factories, government institutions, sports teams and other organizations have more and more often employed diagnostic testing for ensuring safety of working environments and compliance of laws and regulations.

The use of the detecting device for collecting liquid sample such as urine, and determining whether or not special analyte (e.g. drugs and/or metabolites thereof, or markers associated with diseases) exists therein has become a very common method. Such a device generally requires the sample being collected in the sample container, skilled artisans then need to insert a test strip into the sample by submerging a portion of the test strip, subsequently fetch out the test strip to read the result. During this process, those skilled one may directly contact the sample and therefore endanger their health or render the samples contaminated. In order to avoid this risk, a closed lid is required on the sample-collecting container for operation. At present, there are a lot of closed devices, such as the devices disclosed in U.S. Pat. Nos. 4,976,923, 5,429,804 and 6,726,879. These devices include fixing the test strip on the lid of the detecting device, when being used, the container is overturned or tilted to dip the test strip into the sample for detecting. The US Patent Application No. 2003/0027359A1, published on Feb. 6, 2003, discloses a urine detecting cup, which still needs a push-rod to push a column piston to move after the lid covers the opening of the cup, so that the liquid sample flows out from the chamber and contacts the detecting element. The Chinese Patent Application No. 200510113977.5 discloses another urine detecting cup, which initiates the liquid flowing into the detecting chamber from a collecting chamber after the lid covers the opening of the cup so as to start the detecting. Another Chinese Patent Application No. 200480033286.8 also discloses a urine detecting cup, which also starts the detecting after the lid covers the opening of the cup.

Recently, detecting devices have been adopted more and more often by ordinary families or non-professional institutions. Since these detecting devices are designed specially for non-professional persons, their operation processes should be simple and yet they should ensure accuracy of the detecting results.

Accordingly, the detecting devices, which can be operated easily and yet still have accurate and authentic detecting results, are required at present. The object of the present invention is to provide such detecting devices that accord with the above requirements.

SUMMARY OF THE INVENTION

The present invention provides a detecting device which can be operated easily. To be specific, the present invention provides a urine detecting cup which can be operated easily. After the lid of the urine cup is covered onto the opening of the cup, the urine detecting cup further comprises an indication device, which indicates whether or not the lid approaches to and closes at an appointed position. On the one hand, when different operators cover the lid onto the opening of the cup, especially non-professional persons, the degrees of tightness for the lid covering onto the opening of the cup are different for different operators, which may result in that some lids do not completely seal the opening of the cup and these urine detecting cups thus have the possibility of liquid leaking. The present invention provides an indication device on the detecting device, when the lid covers at the appointed position on the collecting chamber (this position is deemed as where the lid totally seals the opening of the collecting chamber), the indication device indicates that the lid has sealed the opening of the collecting chamber and the operator is no longer required to cover the lid. By this way, the openings of devices are all sealed without liquid leaking risk. On the other hand, in some devices, once the lid covers the opening of the collecting chamber, the liquid sample in the collecting chamber starts to contact with the detecting element for detecting. At this time, traditional urine detecting cups need to count the time and read the detecting result displayed on the detecting area of the detecting element after a certain time. When different operators operate, there is no such a unified standard as to what specific time the counting of time should start; thus, for different operators, the same device may result in different detecting results. The present invention provides a detecting device, when the lid approaches to and closes at the appointed position on the collecting chamber, the indication device sends an indication signal, for example, a sound, to notify the operator to start counting the time to be waited for reading the detecting result displayed on the detecting element.

In one aspect, the present invention provides a device for detecting whether or not an analyte exists in the sample, comprising: a collecting chamber containing an opening for collecting liquid sample; a detecting element for detecting the analyte in the liquid sample; and a lid for covering the opening of the collecting chamber, wherein the device further comprises an indication device thereon for indicating whether or not the lid covers at the appointed position.

In some preferred embodiments, when the lid covers at the appointed position, the indicating device indicates that the lid has sealed the opening of the collecting chamber; or, when the lid covers at the appointed position, the indicating device indicates starting to count the time to be waited for reading the detecting result displayed on the detecting element.

In other preferred embodiments, the indicating device indicates by making a sound. In some specific embodiments, the indicating device contains some elements, which collide with each other after undergoing elastic deformation and rebound to make a sound. To be specific, the indicating device contains two elements, after contacting with each other, the two elements or one of the two elements undergoes elastic deformation and then rebound so as to collide with the other one to make a sound. In one specific embodiment, the indicating device contains an elastic element and a non-elastic element, when the elastic element passes by the non-elastic element, the elastic element is pressed by the non-elastic element to undergo the elastic deformation, when the pressing force disappears, the elastic element rebounds to make a sound. The "elastic element" and "non-elastic element" described in the present invention are relative conceptions. In general, the elastic modulus of the elastic element is generally smaller than that of the non-elastic element. For example, the plastic is used as the elastic element, and the metal such as iron, steel, or plumbum is used as the material for the non-elastic element. By the interaction between the plastic and non-elastic element, which gives identical force to each other, the elastic element is relatively easier to be changed in shape since its elastic modulus is smaller than that of non-elastic element; consequently, when the received force suddenly disappears, the elastic element needs to spring back to the original shape so as to knock or oscillate to make a sound. In the present invention, the force received by the elements that are elastically deformed needs to be smaller than the fixed intrinsic elastic limits of said elements. By this way, they can automatically return to their original shapes or status when the outside force disappears. Optionally, both the elastic element and non-elastic element are made of plastic materials.

More preferably, the non-elastic element may be placed on the outer surface of the lid edge; the elastic element may also be placed on the surface of the outer wall of the cup opening. In more specific embodiments, the non-elastic element may protrude from the outer wall, containing a gradually heightened sliding surface, in the process where the lid rotates relative to the cup to seal the opening, the elastic element slides gradually from a low position to a high position of the sliding surface. Consequently, when the elastic element passes by the protruding non-elastic element, the elastic element is forced by the protruding element to deform and then rebound to knock the lid.

In other specific embodiments, the non-elastic element is placed on a substrate sheet which can be elastically deformed. There are various ways by which the substrate sheet is easy to be elastically deformed. In a specific embodiment, both ends of the substrate sheet connect the lid edge, and the width of one end connecting the lid edge is larger than that of the other end connecting the lid edge. Besides, the elastic element and collecting chamber can move synchronously in a counter-clockwise direction relative to the lid, and the non-elastic element and lid can move synchronously in a clockwise direction relative to the collecting chamber.

In an optional embodiment, the substrate sheet can be rectangle, with a rectangle gap lying along the long side, separating the sheet from the lid edge. In another optional embodiment, the elastic element interacts with the non-elastic element on the substrate sheet, the elastic element and the substrate sheet are elastically deformed synchronously; when the interaction force disappears, the elastic element and the substrate sheet collide with each other to make a sound.

In yet other specific embodiments, the non-elastic element is made of acrylonitrile-butadiene-styrene copolymer material, and the elastic element is made of polypropylene material. Optionally, the elastic element passes by the non-elastic element and knocks the lid, and then the elastic element is prevented by the non-elastic element from moving clockwisely relative to the lid. In another optional embodiment, the elastic element passes by the non-elastic element and knocks the lid, and then the elastic element can still move clockwisely relative to the lid. Optionally, the way that the lid covers the opening of the collecting chamber is through rotating the lid around the chamber opening to seal the opening; the opening contains an external screw thread, and the lid contains an internal screw thread, the two screw threads match with each other. In an optional embodiment, the elastic element can be placed on the lid; the non-elastic element can be placed on the collecting chamber. In a preferred embodiment, the elastic element is placed on the surface of the outer wall of the lid and the non-elastic element is placed on the surface of the outer wall of the collecting chamber.

In another aspect, the present invention provides a method for detecting an analyte in a sample, comprising, providing a detecting device, which comprises a collecting chamber containing an opening for collecting liquid sample, a detecting element for detecting an analyte in the liquid sample, and a lid for covering the opening of the collecting chamber; covering the lid onto the opening of the collecting chamber so that an indicating device on the detecting device will indicate whether or not the lid covers at the appointed position. In an embodiment, the indicating device indicates by making a sound. In another embodiment, once the indication is received from the indicating device, the lid is stopped from further movement to seal the opening of the collecting chamber. In a specific embodiment, the lid seals the opening of the collecting chamber by means of rotation; once the indication is received from the indicating device, the lid is stopped from rotating. In addition, in another embodiment, once the indication is received from the indicating device, the time to be waited for reading the detecting result displayed on the detecting element starts to be counted. In yet another embodiment, once the indication is received from the indicating device, the time to be waited for reading the detecting result displayed on the detecting element starts to be counted, and at the same time, the lid is stopped from rotating.

In other preferred embodiments, the present invention provides a method for detecting an analyte in the sample, comprising: providing a detecting device containing a collecting chamber with an opening; a detecting element; and a lid rotating relative to the collecting chamber to seal the opening, wherein the device further comprises an indicating device for indicating whether or not the lid rotates to an appointed position; rotating the lid until the indicating device makes a sound.

In some preferred embodiments, when the indicating device sends an indication, the rotation is stopped. Optionally, when the indicating device sends an indication, the time to be waited for reading the detecting result displayed on the detecting element starts to be counted. In one specific embodiment, the indicating device indicates by making a sound. More preferably, the indicating device contains an elastic element protruding from the outer surface of the collecting chamber and a non-elastic element protruding from the outer surface of the lid edge. During the process of rotating the lid, the elastic element is pressed by the non-elastic element to undergo deformation and then rebound to knock the lid edge to make a sound. Most preferably, the non-elastic element comprises a gradually heightened sliding surface, so that the elastic element slides gradually from a low position to a high position on the sliding surface, and then suddenly moves from the high position to the lid edge and knocks the lid edge to make a sound.

The device and method of the present invention render operation of the detecting device easier, which are more suitable for non-professionals; further, the detecting result provided therein is more accurate.

BRIEF DESCRIPTION OF THE DRAWINGS

FIGS. 6A-6D is a sketch diagram of the operation principle of the indicating device illustrating how the indicating device indicates by making a sound in a specific embodiment of the present invention.

REMARKS OF THE REFERENCE SIGNS

Figure 1:
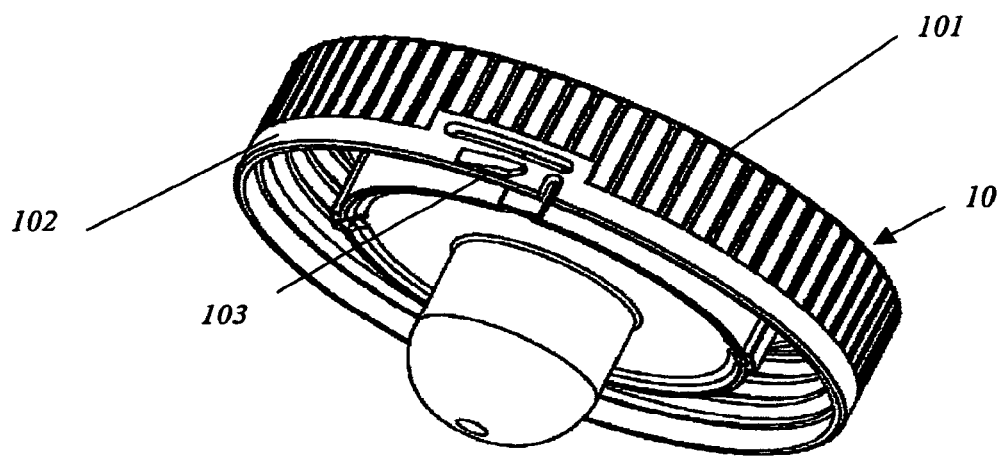
FIG. 1 is a sketch diagram of stereo structure of the lid in a specific embodiment of the present invention, a part of structure of the indicating device is positioned on the outer surface of the edge of the lid.

Lid 10; collecting chamber 202; cup 20; opening of the collecting chamber 201, side wall of the collecting chamber 210; detecting chamber 207, bottom of the collecting chamber 206; elastic element 204; periphery edge 203; outside surface 208; inside surface 209; detecting device 100; indicating device 30; non-elastic element 103; lid edge 101; outer surface of the lid edge 102; sliding surface 107; substrate sheet 104; basal end of the substrate sheet 109; top end of the substrate sheet 111; top long side of the substrate sheet 114; bottom long side of the substrate sheet 113; connection portion 112; gap 105; gap 106; basal connection portion of the substrate sheet 115; slope of the non-elastic element 22; slope of the elastic element 40.

DETAILED DESCRIPTION OF THE INVENTION

The structures or the used technical terms related in the present invention are further described below.

Detecting

Detecting means assaying or testing whether or not a substance or material exists, for example, but not limited to, chemical substances, organic compounds, inorganic compounds, metabolic products, drugs or drug metabolites, organic tissues or metabolites of the organic tissues, nucleic acids, proteins or polymers. Detecting also means to determine the quantities of the substances or materials. Furthermore, detecting also includes assays, including immune assays, chemical assays and enzyme assays and the like.

Detecting Device

In a specific example, the detecting device comprises a collecting chamber 202 for collecting and storing liquid sample, the collecting chamber being formed by a side wall 210 and a bottom 206, and an opening 201 for accepting the liquid sample. The word "a" used herein, including the Description, abstract and claims of the present application, should be understood as at least one, or the number involved therein containing one, and should not be only understood as "unique" or "only one". For example, the detecting device comprises an indicating device, obviously, the detecting device comprising two or more indicating devices also fall into the scope of protection of the present claims and should not be excluded therefrom. The detecting device further comprises a detecting chamber 207 containing a detecting element, the liquid sample in the collecting chamber may be freely or under controlled in contacting with the detecting element in the detecting chamber; the chemical reagent on the detecting element may detect whether or not the analyte exists in the liquid sample or the quantities of the analyte existing therein. The detecting device further includes a lid 10 to cover the opening 201 of the collecting chamber. In a specific embodiment, the detecting device contains an indicating device 30 for indicating whether or not the lid covers at the appointed position, in particular, whether or not the lid covers at the appointed position on the collecting chamber. On the one hand, when the lid covers at the appointed position on the collecting chamber, the indicating device indicates that the lid has totally sealed the opening of the collecting chamber. On the other hand, when the lid covers at the appointed position of the collecting chamber, the indicating device indicates to start counting the time to be waited for reading the detecting result displayed on the detecting element. The ways that the lid covers the collecting chamber are various, e.g. covering by matching of screw threads. For example, the opening of the collecting chamber contains an external screw thread, and the lid contains an internal screw thread that matches the said external screw thread of the opening; when the lid is covered onto the collecting chamber, it seals the opening by rotation relative to the chamber. In addition, the lid can be inserted into the opening to seal the opening by taking the form of piston.

The indicating device of the present invention can also be applied to other detecting devices, especially to those devices that contain a lid and use the lid to seal the opening of the collecting chamber. These similar devices have been disclosed and described, for example, in U.S. Pat. Nos. 7,270,959, 7,300,633, 7,560,272, 7,438,852, 4,976,923, 5,429,804, and 6,726,879, all of which are hereby incorporated by reference in their entirety, and the detecting devices disclosed in these references can be combined with the indicating device disclosed in the present invention as one of the specific embodiments of the present invention.

Indicating Device

In a specific embodiment, the indicating device 30 may be positioned on the detecting device, the indicating device indicates by making a sound. Such a sound may be "pa," "peng," "dong," "ding-ling," "pi-pa," or any other suitable sound.

In some embodiments, the lid rotates relative to collecting chamber to seal the opening, a part of the indicating device is positioned on the lid and the other part of the indicating device is positioned on the wall of the collecting chamber; when the lid rotates to seal the opening, the part of the indicating device positioned on the lid and the other part of the indicating device positioned on the collecting chamber undergo elastically deformation by interaction with each other, when the interaction force disappears, the elastically deformed parts collide with each other to make a sound. In particular, the indicating device can contain an elastic element and a non-elastic element. For example, the urine detecting cup as shown in FIGS. 1-6, contains a lid 10 and a collecting chamber 20. The lid contains a lid edge 101 having an element 103 on its outer surface 102, and this element can be substantive non-elastic element. At the same time, the collecting chamber contains an element 204 on its outside wall close to the opening 201 of the cup, this element can be substantive elastic element; the elastic element 204 is upright in parallel with the outside wall 210 of the collecting chamber and is positioned at a certain distance from the outside wall; the elastic element has a certain thickness, may be 1-5 mm, with an outside surface 208 and an opposite inside surface 209. When the lid is covered onto the opening, at first the inside surface 209 is slightly in contact with the outside surface 102 of the lid edge. When the elastic element 204 is pushed by a force vertical to the inside surface 209 and away from the side wall of the collecting chamber, the elastic element bends or twists outward from the collecting chamber wall 210; if the force vertical to the inside surface suddenly disappears, the elastic element has to restore to the initial state under the action of its own stress, during the process of resuming from deformed state to the initial state, the inside surface 209 of the elastic element rapidly knocks the outer surface 102 of the lid edge and consequently make a sound.

Figure 2:
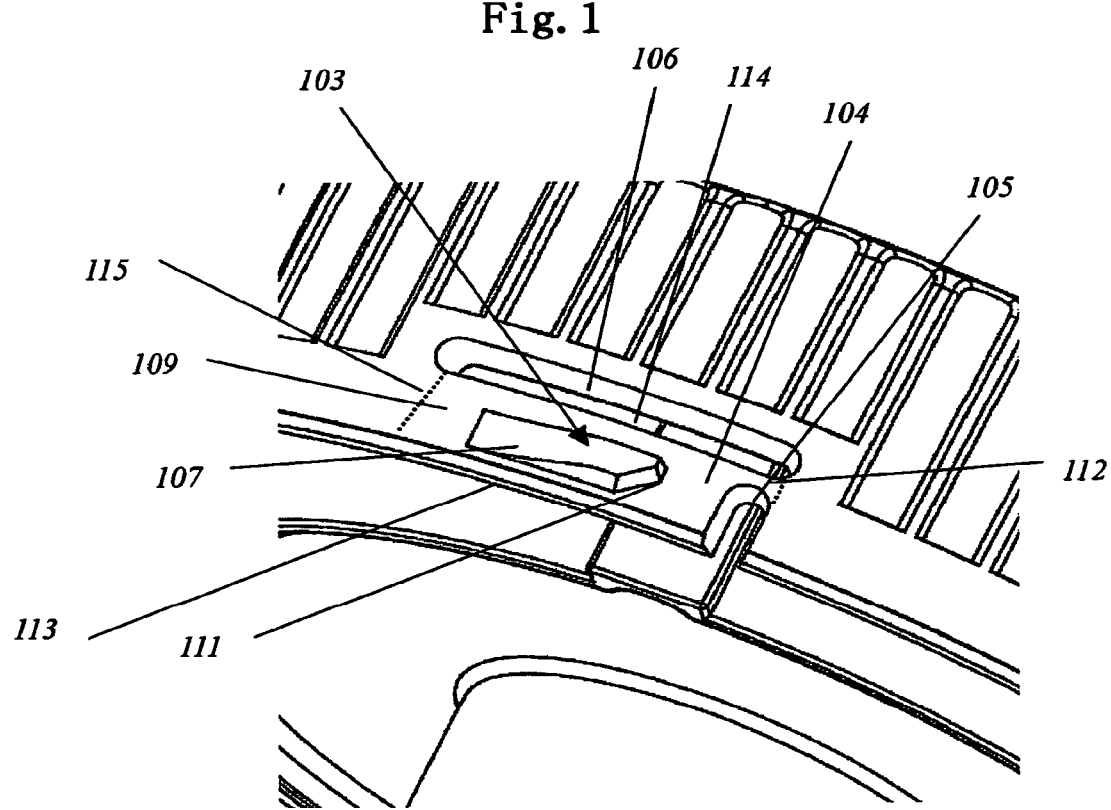
FIG. 2 is an enlarged sketch diagram of a part of the indicating device on the lid edge in a specific embodiment of the present invention.

In some more preferred embodiments, the protruding element 103 positioned on the lid can be made of substantive non-elastic material, directly protruding outward from the outer surface 102 of the lid edge 101, the protruding element 103 is in the shape of a sliding slope and contains a sliding surface 107. As shown in FIG. 2, if the lid seals the opening by rotating clockwisely relative to the opening, the sliding surface 107 gradually moves from a low position to a high position in the counter-clockwise direction, the sliding surface in low position extends from the outer surface of the lid edge, the end of the sliding surface in high position has a certain vertical distance d from the outer surface of the lid edge, e.g. a distance in the range from 1 mm to 10 mm. As shown in FIG. 6, during the process of use, when the lid rotates clockwisely to seal the opening, when the lid almost reaches to the appointed position, the inside surface 209 of the elastic element on the opening starts approaching the outer surface of the lid edge, and at this time, it may slightly contact the outer surface as shown in FIG. 6A. Subsequently, the elastic element slides on the sliding surface 107 of the protruding element 103 and slides from the lowest position to the highest position along the sliding surface as shown in FIG. 6B; at the same time, the elastic element bends in the direction away from the outer wall of the collecting chamber accompanying the sliding, and undergoes elastically deformation, as shown in FIG. 6B by the upright arrow. When the inside surface 209 slides to the highest position of the protruding element, the elastic element reaches to a maximum bending, as shown in FIG. 6C. However, the force received by the elastic element does not go beyond its own elasticity limit; thus, accompanying with continuous rotation of the lid, the elastic element 204 rapidly slides out from the sliding surface 107 and suddenly loses the support of the sliding surface 107, therefore moving rapidly towards the lid edge under its own elastic property and knocking the lid edge to make a sound, as shown in FIG. 6D, indicating the operator that the lid has rotated to the appointed position, and the lid has sealed the opening of the collecting chamber, there is thus no need for rotation further more. Optionally, it can indicate the operator to start counting the time to be waited for reading the detecting result displayed on the detecting element. Indicating the operator that the lid has rotated to the appointed position and that the time to be waited shall start to be counted can be progressed simultaneously or separately. The indication that the lid has reached to the appointed position can be given various meanings, e.g., making a sound can mean starting the next step, or starting the detection, or finishing the detection, or any other steps that may need to be indicated. All of these can be described in the instruction manual of the product, instructing the operator to understand the meaning of the indication. Furthermore, the elastic element and non-elastic element in the indicating device can be separately manufactured from the other parts of the detecting device, and then the elastic element can be fixed on the outer wall surface of the collecting chamber, especially the place close to the opening, and the non-elastic element can be fixed on the outer surface of the lid edge, both by means of adhesion. Even more preferably, the collecting chamber and lid can be injection molded by a die in one step by using different materials, e.g., the lid is injection molded by using acrylonitrile-butadiene-styrene copolymer (ABS), and the collecting chamber is injection molded by using Polypropylene (PP) material.

"Appointed position" can be pre-arranged, for example, when the lid rotates to seal the collecting chamber, it can be set as the fixed number of circles that the lid to be rotated from the initial contact position, e.g. 1-5 circles, when lid can be deemed to completely seal the opening of the collecting chamber. Specifically, an inner screw thread is placed on the lid, an external screw thread is placed on the collecting chamber, both the inner screw thread and external screw thread are provided with interfaces for matching with each other, once they match with each other, the lid and the collecting chamber are effectively rotated and the lid moves from a high position to a low position; an elastic seal ring is generally provided inside the lid, when the elastic seal ring is in contact with the opening of the cup, it is needed to further rotated 0.1-1 circles so that the seal ring is in tight contact with the opening of the cup, which means total sealing. When the position of the inner screw thread and the non-elastic element is fixed on the lid, the position of the elastic element on the collecting chamber can be easily determined by arranging the number of circles of the screw thread and the pitch of the screw thread so that after rotating the lid a certain circles, when the seal ring is just about to seal the opening, the elastic element interacts with the non-elastic element and makes a sound for effective indication, suggesting that the lid has effectively sealed the opening and no more rotation is needed. Aside from the aforementioned way, there are other optional ways that can be used for arranging the appointed position. "Appointed position" in the present invention can refer to not only the position where the lid totally seals the collecting chamber but also the position where the detecting device starts the detection assay. For example, the device can be set so that the detecting device starts the detection assay as long as the lid rotates to a certain position; thus, when the lid rotates to the appointed position, the indicating device makes a sound for indicating the beginning of the assay. Optionally, in other ways, the elastic element can also be positioned on the lid and the non-elastic element positioned on the outside wall of the collecting chamber.

In some more preferable embodiments, the protruding element 103 is positioned on a substrate sheet 104 that can be elastically deformed, the substrate sheet may be a part of the lid edge 101, as shown between the broken lines in FIG. 2, and can be substantially a rectangle. In a preferable embodiment, the long side 114 of the substrate sheet is not connected with the lid edge, a rectangle gap 106 may be formed between the long side 114 of the substrate sheet and the lid edge, and the length of the gap is substantially equivalent to the length of the substrate sheet, or slightly less than the length of the substrate sheet. Such arrangement will impart better elasticity to the substrate sheet so that it can be easily deformed under the interaction force; moreover, the elastic element can\knock the top end of the substrate sheet to make a much more clear and clangorous sound. When the elastic element 204 on the collecting chamber presses down the non-elastic element 107 on the lid edge, since the substrate sheet has certain elasticity, it also undergoes elastic deformation under the interaction of the force. When the protruded elastic element 204 knocks the top end 111 of the substrate sheet, the substrate sheet and the elastic element collide with each other, since the substrate sheet may decrease the influence of the lid on the vibration, this may result in a much more clear and clangorous sound.

In another more preferable embodiment, the basal end 109 of the substrate sheet is connected with the lid edge, and the top end 110 of the substrate sheet is connected with the lid edge via a connection 112; at the same time, the width of the connection 112, through which the top end 110 connects with the lid edge, is smaller than the width of the connection part through which the basal end connects with the lid edge, so that a gap 105 is formed between the top end of the substrate sheet and the lid edge. In this way, the substrate sheet can be easily deformed elastically under the interaction between the elastic element 204 and the protruding element 103 so as to make a much more clear and clangorous sound.

Figure 7A:
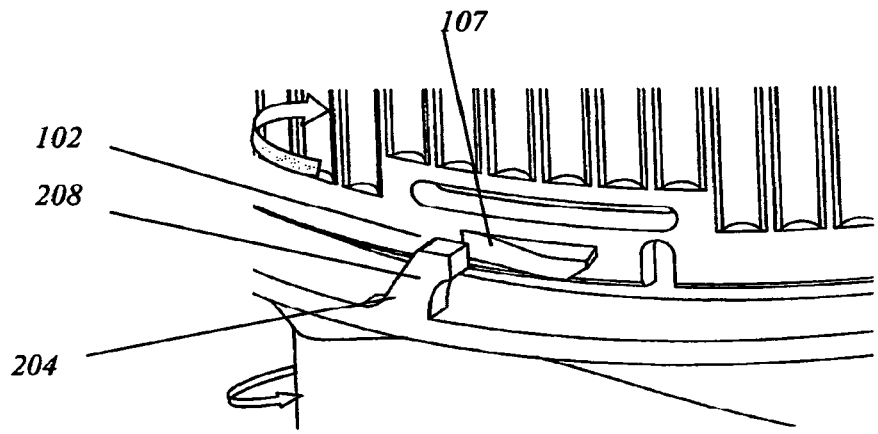
FIGS. 7A-7C is a sketch diagram illustrating how the indicating device structure is involved in the process of making a sound for indication in a specific embodiment of the present invention.
Figure 7B:
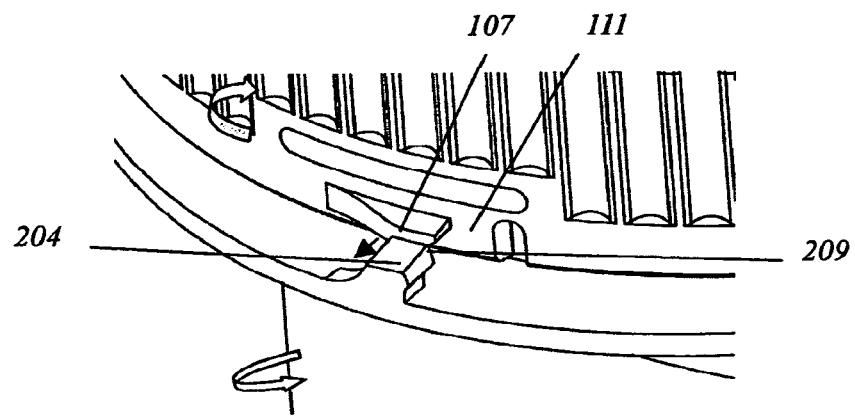
Figure 7C:
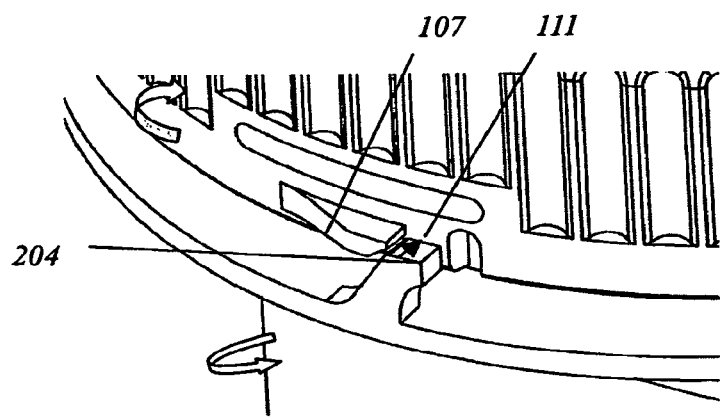

In another optional embodiment, after the elastic element 204 moves on the surface of the protruding element 103 and knocks the lid edge to make a sound, the lid and the collecting chamber can no longer moved relative to each other, but fixed at a position and in a locked state. In a specific embodiment, after the lid seals the opening, the lid cannot be rotated reversely to open the opening. One of the ways to fix the lid is that the non-elastic element 104 prevents the elastic element from rotating reversely; for example, the lid 10 rotates clockwisely to seal the opening 201, after the indicating device 30 makes an indication, since the non-elastic element has a surface vertical to the lid edge so that it stops the elastic element from moving backwards, the elastic element thus cannot be rotated counter-clockwisely, as shown in FIG. 7C or FIG. 6D. In this way, the lid and collecting chamber are in a locked state. "Locked state" in the present invention means that the lid and collecting chamber are fixed together as a whole, the lid cannot move relative to the opening of the collecting chamber, including both continuous rotation of the lid for sealing the opening of the collecting chamber and reversed rotation of the lid for opening the opening of the collecting chamber.

Figure 8A:
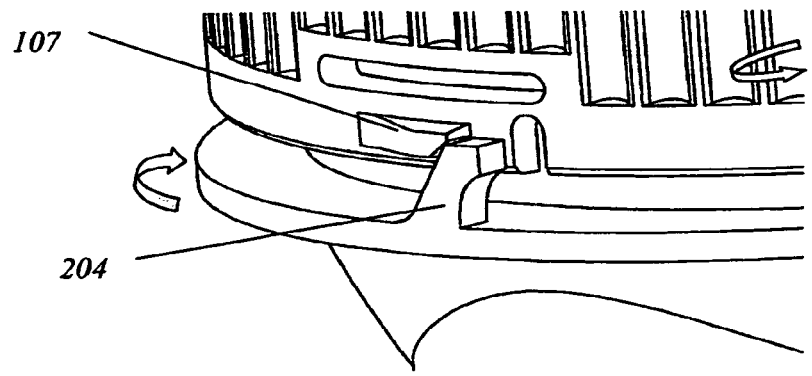
FIGS. 8A-8C is a sketch diagram illustrating how the indicating device structure is involved in the process of opening the lid for the result confirmation after the indication in a specific embodiment of the present invention.
Figure 8B:
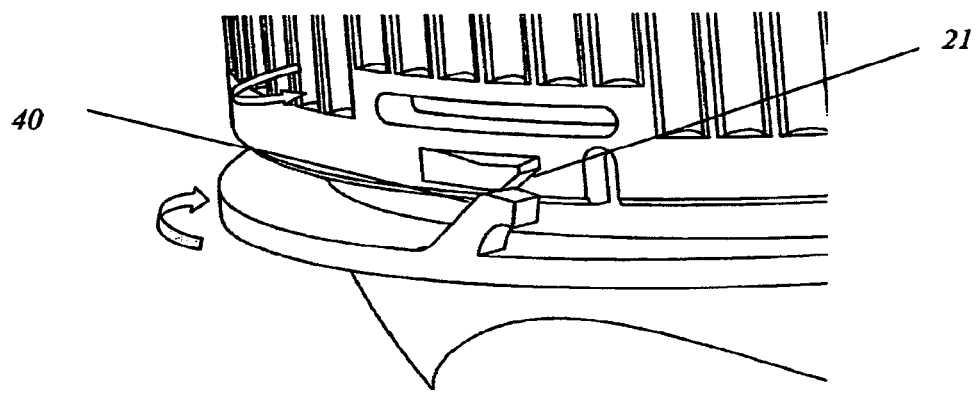
Figure 8C:
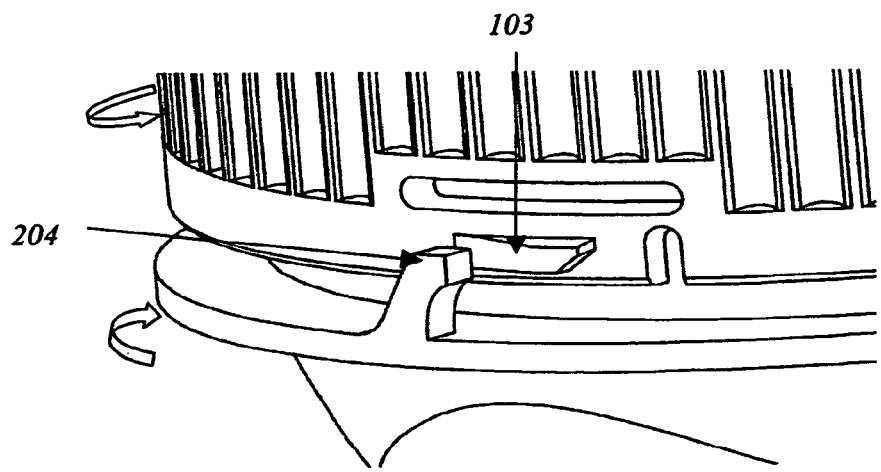

In another optional embodiment, after the elastic element 204 moves on the surface of the protruding element 103 and knocks the lid edge to make a sound, the movements of the lid and collecting chamber can be reversed to open the opening of the collecting chamber. For example, when the operator rotates the lid to the appointed position, upon hearing a sound of "pa" made by the indicating device, he/she stops further rotating the lid, this sound indicates that the lid has been placed at the position for sealing the opening of the collecting chamber. At this time, other operations can be undertaken to detect the analyte in the sample. Of course, upon hearing the indication sound made by the indicating device, the operator can also start to count the time to be waited for reading the detecting result displayed on the detecting element, e.g., the operator starts reading the detecting result displayed on the detecting element after waiting for example 2-5 minutes. Reading means directly observing changes of the color or the shade of color on the detecting element by naked eyes to determine whether or not the analyte exists or the quantities of the analyte therein, or directly reading and automatically outputting the results by a machine. After finishing these operations, for example, if finishing the detection and finding that the detecting result is positive, the sample in the detective device is to be delivered to the professional institution, where the operator needs to rotate the lid reversely to open the collecting chamber and extract the sample for confirmation. In order to facilitate reverse rotation of the lid, in a specific embodiment, as shown in FIG. 8, the non-elastic element contains an slope 21 being in contact with an slope 40 on the elastic element, when the lid is reversely rotated, since the elastic element 204 has elasticity, its slope 40 receives a force from non-elastic element and consequently bends downwards, so that the lid can successfully rotate reversely to open the opening of the collecting chamber.

Detecting Method

The present invention provides a method for detecting analyte in the sample, comprising: providing a detecting device 100, which comprises: a collecting chamber 202 including an opening 201 for collecting liquid sample, a detecting element for detecting analyte in the liquid sample, and a lid 10 for covering the opening of the collecting chamber; when the lid is covered onto the opening of the collecting chamber, an indicating device 30 on the detecting device indicates whether or not the lid has covered at the appointed position. In an embodiment, the indicating device makes a sound to indicate. In another embodiment, once the indicating device sends an indication, the lid is stopped from being moving further onto the opening of the collecting chamber. In a specific embodiment, the lid seals the opening of the collecting chamber by means of rotating, once the indicating device sends an indication, the lid is stopped from being further rotated. Moreover, in another specific embodiment, once the indicating device sends an indication, the time to be waited for reading the detecting result displayed on the detecting element starts to be counted. In yet another specific embodiment, once the indicating device sends an indication, the time to be waited for reading the detecting result displayed on the detecting element starts to be counted calculated and, at the same time, the lid is stopped from being further rotated.

Detecting Element

Various detecting elements may be combined together and applied to the present invention. One form is the test strip. The test strips used for analyzing an analyte (e.g., drugs or body metabolites) in a sample have various kinds, such as the kind for immunoassay or chemical assay. The test strip can adopt the analysis mode of noncompetitive method or competitive method. A typical test strip can contain a water-absorbing sample-adding area, a reagent area, and a test area. Adding the sample to the sample-adding area and the sample flows into the test area via capillary action; if the analytes exist, the sample binds the reagents in the reagent area, and then the sample continues to flow into the test area; other reagents, such as molecules specifically binding the analytes are fixed in the test area, these reagents react with the analytes (if exist) in the sample and bind the analytes in this area, or bind a reagent from the reagent area. Markers for showing the detecting signal are in the reagent area or a separated label area.

The typical analysis mode of noncompetitive method is: if the sample contains the analyte, the signal is generated, if the sample does not contain the analyte, the signal will not be generated, whereas in competitive method, if the analyte does not exist in the sample, the signal is generated, if the analyte exists in the sample, the signal will not be generated.

The detecting element can be the test strip that is made from absorbent or nonabsorbent materials. The test strip may contain several materials for delivering the liquid sample; one material may cover onto the other material, e.g., the filter paper may cover onto the nitrocellulose membrane. One area of the test paper may contain one or more materials, whereas another area may contains one or more different materials. The test paper can be adhered to a certain support or hard surface for enhancing the strength of the test paper for handling.

The analyte is detected via a signal-generating system. For example, one or more enzymes specifically react with the analyte; thus, they could be used to make the signal-generating systems that are fixed on the test area of the test strip by using the above described methods. The substances that can generate signals may be on the sample-adding area, reagent area, test area, or the entire test strip, and these substances may fill in one or more materials used in the test strip. Adding the solution containing signal substances onto the surface of the test strip or immerging one or more materials of the test strip into the solution containing signal substances, then drying the test strip with the solution containing signal substances.

The areas of the test strip can be arranged in the following way: sample-adding area, reagent area, test area, control area, an area determining whether or not the sample is adulterated, and finally a sample absorbing area; the control area is positioned behind the test area. All of the above areas can be arranged on one test strip made of only one material, or different areas can adopt different materials. Each area can contact with the liquid sample directly, or different areas can be arranged according to the flowing direction of the liquid sample, with each area being connected to and overlapped with the other area. The materials used in the test strip may be those having good water absorption capability, such as filter paper, glass fiber or nitrocellulose membrane and the like. The test strip may adopt other forms, too.

Types of the Sample.

Any types of samples can be applied to the device of the present invention for test, comprising body fluid (e.g. urine and other body fluids and clinical samples). The liquid samples may be samples from solid orsemi-solid samples, comprising dungs, biological tissues and food samples. These solid or semi-solid samples can be converted into liquid samples by any suitable methods, for example, the solid samples (e.g. water, phosphate buffer or other buffers) are mixed, macerated, incubated, dissolved or subjected to enzymatic hydrolysis in a suitable liquid. The "biological samples" contains samples from living animals, plants and food, also contains urine, saliva, blood and blood ingredients, cerebrospinal fluid, vaginal swab, seminal fluid, sweat, secretion, tissue, organ, tumor, culture of tissues and organs, cell culture and medium therein, regardless whether they are from human beings or animals. The food samples contain processed food ingredients and final products, such as meat, cheese, alcohol, milk and drinking water. The plant samples contains samples from any plants, plant tissues, plant cell cultures and mediums therein. "Environmental samples" contains samples from environment (e.g. sample of lake water or samples of other water, sewage sample, soil sample, groundwater sample, sea water sample and samples of rubbish and waste water). The sewage and relevant rubbish can also be contained in the environmental samples.

Type of the Analyte

The present invention can be used for analyzing any analyte. Examples of the analyte that can be detected stably by the present invention comprise (but not limited to) human chorionic gonadotrophin (hCG), luteinizing hormone (LH), follicle-stimulating hormone (FSH), hepatitis C virus (HCV), hepatitis B virus (HBV), Hepatitis B virus surface antigen, AIDS virus and any drugs of abuse. The analyte can be detected in any liquid or liquefied samples, for example, urine, saliva, slobber, blood, plasma or serum. Other examples of the analytes also include, creatinine, bilirubin, nitrite, (non-specific) proteins, blood, leucocyte, blood glucose, heavy metals and toxins, bacterial components (e.g. special proteins and saccharides of the bacterium of particular type, e.g., *E. coli* 0157:H7, *Staphyloccocus aureus*, *Salmonella*, *Clostridium perfingens*, *Campylobacter*, *Listeria monocytogenes*, *Vibrio parahaemolyticus*, or *Bacillus cereus*). Any other analytes suitable for side-stream test can be detected by this device. The analyte can be infectious substances or the substance that can indicate the infection period. The analyte can be drugs (e.g. drugs of abuse), hormones, proteins, nucleic acid molecules, pathogens. "Drug of Abuse" (DOA) refers to using drugs (typically for paralyzing nerves) for non-medical purpose. Abuse of these drugs will cause the damage to the body and nerves so as to generate dependency, addiction and/or death. Examples of drugs of abuse include cocain, amphetamine (such as Black Beauty, white amphetamine tablets, dexamphetamine, dextro-amphetamine tablets, Beans); methyl amphetamine (crank, methamphetamine, crystal, speed); barbiturate (such as Valium®, Roche pharmaceuticals, Nutley, New Jersey); sedative (drugs for assisting sleeping); lysergic acid diethylamide (LSD); depressants (downers, goofballs, barbs, blue devils, yellow jackets, methaqualone); tricyclic antidepressants (TCA, i.e., imipramine, amitriptyline and doxepin); phencyclidine (PCP), tetrahydrocannabinol (THC, pot, dope, hash, weed, and etc.); opiates (i.e., morphia, opium, codein, heroin, dihydrohydroxycodeinone). This test strip can also be used to detect drugs which are for medical purposes but are easily overdosed, such as tricyclic antidepressants (imipramine or analogs) and acetyl aminophenol.

The method may include adding a washing step or steps to remove non-nucleic acid molecules, for example salts, from the solid-support-target nucleic acid complex or surrounding solution. Non-nucleic acid molecules are then removed with an alcohol-based wash and the target nucleic acid is eluted under low- or no-salt conditions (TE buffer or water) in small volumes, ready for immediate use without further concentration. In another embodiment, extraction is improved by the introduction of a carrier such as tRNA, glycogen, polyA RNA, dextran blue, linear poly acrylamide (LPA), or any material that increases the recovery of nucleic acid. The carriers may be added to the second binding solution or washing buffer.

EXAMPLES

Examples provided as follows will further describe the present invention, but in any case, they cannot be understood as limitations to the scope of the present invention.

Figure 3:
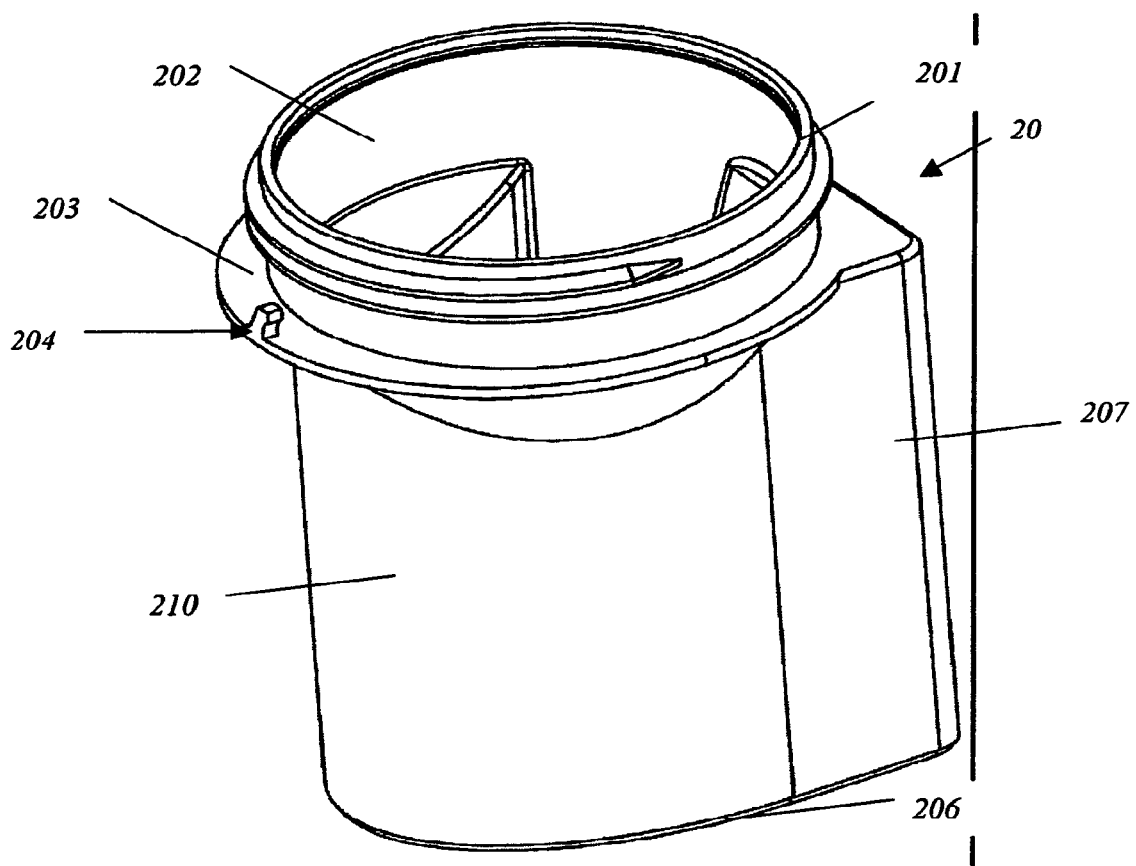
FIG. 3 is a sketch diagram of stereo structure of the collecting chamber in a specific embodiment of the present invention, a part of the indicating device is positioned on the outer surface of the collecting chamber, close to the opening of the cup.
Figure 4:
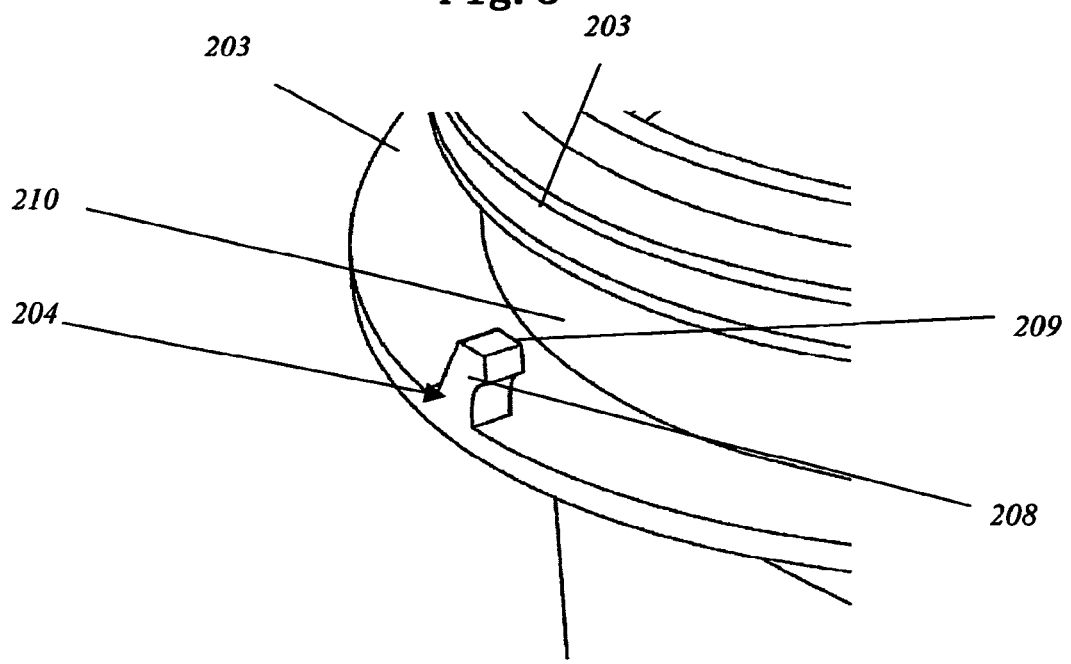
FIG. 4 is an enlarged sketch diagram of the stereo structure of the part of the indicating device positioned on the outer surface of the collecting chamber in a specific embodiment of the present invention.
Figure 5:
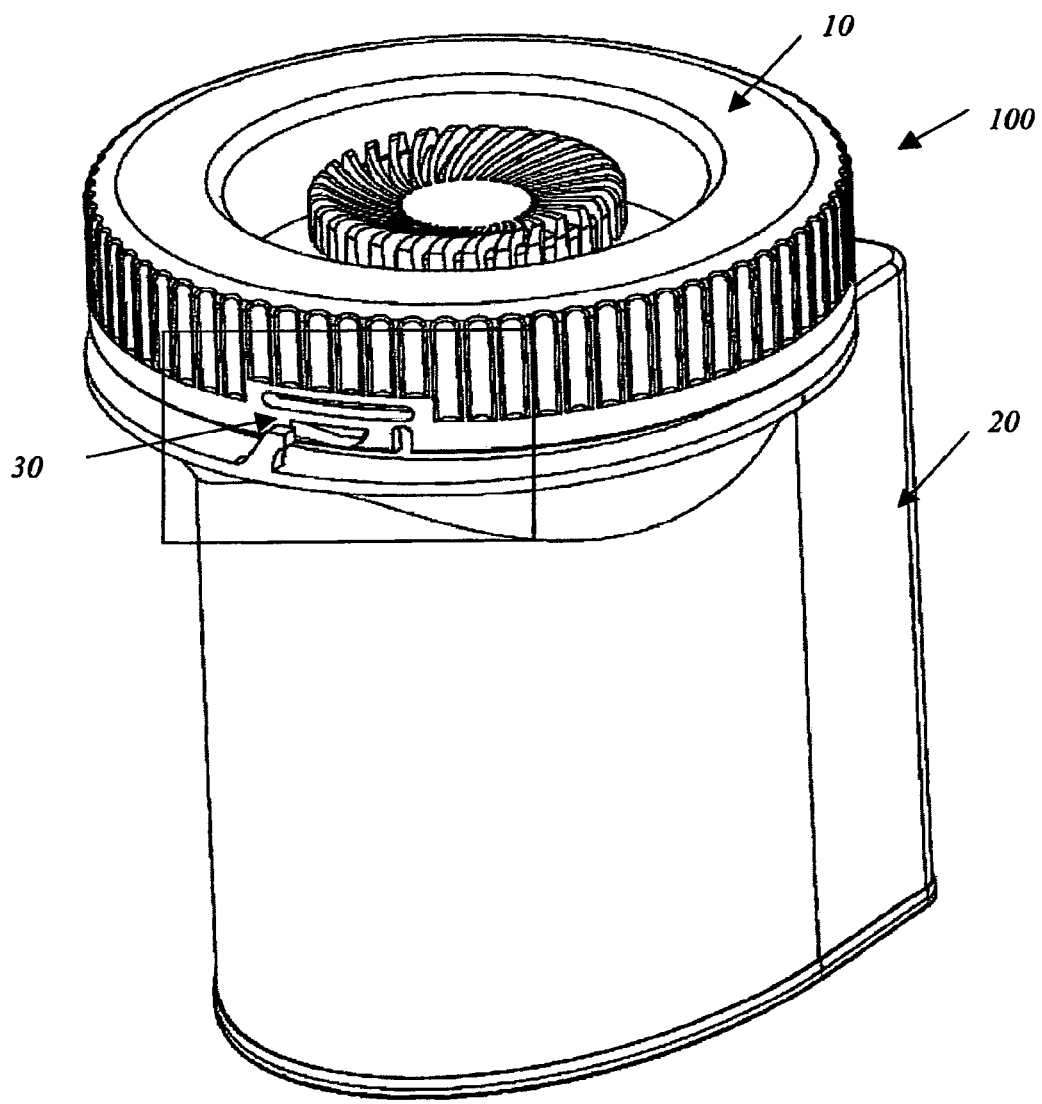
FIG. 5 is a sketch diagram of stereo structure of the detecting device in a specific embodiment of the present invention.
Figure 9:
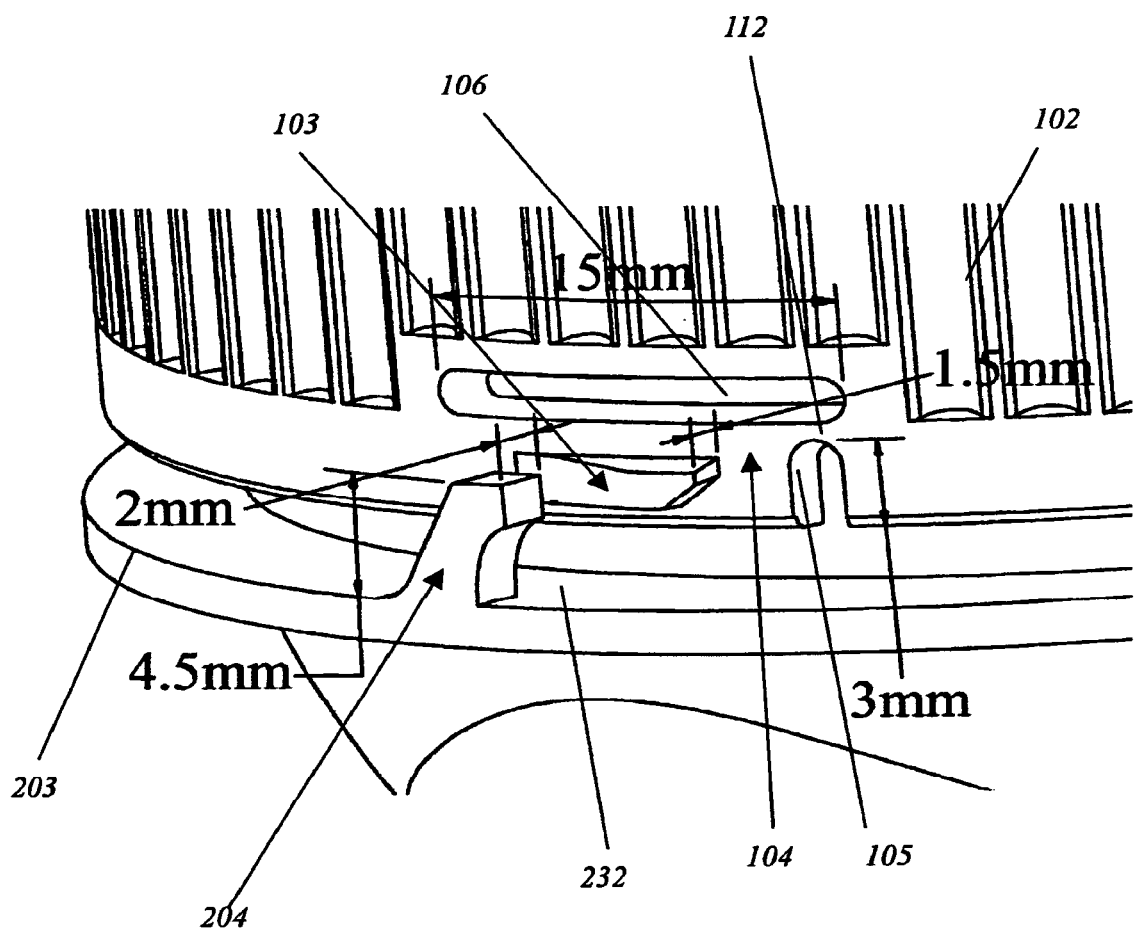
FIG. 9 is an enlarged sketch diagram of the structures of a part of the indicating device in a specific embodiment of the present invention.

Experiment 1. Manufacturing and Assembly of a Detecting Device with an Indication Function As illustrated in FIG. 3 and FIG. 9, the cup 20, which has the elastic element 204 on the collecting chamber 202, is injection molded by a die in one step, and is made of polypropylene material, wherein the collecting chamber is used for collecting the liquid sample, the detecting chamber 27 is connected to the collecting chamber at bottoms, an external screw thread is provided close to the opening of the cup, a ring of protruding periphery edge 203 is provided under the lower end of the screw thread, an elastic element 204 is provided on the edge of the protruding periphery edge 203 (having a width of 4 mm), the top end of this elastic element has a distance of about 4.5 mm from the periphery edge plane 232, the thickness of the elastic element is about 2 mm. As illustrated in FIG. 1, FIG. 2, and FIG. 9, lid 10, non-elastic element 103 and substrate sheet 104 are all made of acrylonitrile-butadiene-styrene copolymer, and are injection molded in one step; the substrate sheet has a length of 15 mm and a width of 5 mm, a gap 106 having a width of 3 mm and a length of 13 mm is formed along the longitudinal direction of the substrate sheet, separating the substrate sheet from the lid edge 102, the top end 111 of the substrate sheet is connected with the lid edge via a connection having a width of 2 mm, the remaining portion is again a gap 105 having a length of 3 mm. The non-elastic element 103 on the substrate sheet is of a sliding platform shape, the highest point of the sliding surface has a distance of 1.5 mm from the surface of the substrate sheet. The thickness of the lid edge is about 2 mm. An inner screw thread matched the external screw thread of the opening of the collecting chamber is provided on the lid edge. The assembly of the molded detecting device is illustrated as shown in FIG. 5.

Experiment 2. Detecting Drug in Urine by a Detecting Device with an Indication Function Collecting the urine with the cup disclosed in Experiment 1, and storing the urine in the collecting chamber 202, then rotating the lid onto the opening, conducting the detection for 50 times in total. Including an explicit instruction in the operation manual: stop rotating the lid upon hearing the sound of "pa", at the same time, start counting the time to be waited for reading the detecting result displayed on the detecting element, which are 5 minutes. Each time the operation was conducted by a nonprofessional, and all the results are evaluated and compared at the end of the experiment. The experiment results show that in all 50 tests, each urine cup is totally sealed without leaking the urine; furthermore, 100% of the detecting results of the experiments are consistent with the result obtained by a traditional detecting device; and these non-professional persons are 99% pleased with the operation of this device, considering that the operation is simple and quick.

The invention claimed is:
1. A device for detecting an analyte in a liquid sample, comprising:
   a) a collecting chamber having an opening for collecting the liquid sample and external screw threads disposed proximate the opening;
   b) a detecting chamber having a detecting element for detecting the analyte in the liquid sample;
   c) a lid for covering the opening of the collecting chamber, the lid having a circumferential lid edge comprising an outer surface extending circumferentially around the lid and internal screw threads that rotationally engage the external screw threads of the collecting chamber; and
   d) an indicating device configured to indicate whether the lid covers the opening at an appointed position at which a liquid tight seal of the opening is formed when the lid and the collecting chamber are rotated relative to each other to close the collecting chamber,
   wherein the indicating device comprises an elastic element having an elastic modulus for elastic deformation, the elastic element disposed on the collecting chamber and a non-elastic element disposed on the outer surface of the lid edge,
   wherein the indicating device generates a knocking sound when the lid covers the opening at the appointed positions, the knocking sound resulting from elastic deformation and rebound of the elastic element disposed on the collecting chamber upon interaction with the non-elastic element disposed on the lid edge,
   wherein the non-elastic element has a length that extends along the outer surface partially around the lid and the elastic element and the non-elastic element are in rotatable engagement with the internal and external screw threads,
   wherein the elastic element is pressed by the non-elastic element when engaged during rotation to close the detecting chamber and undergoes elastic deformation and then rebounds to return to its original shape and status thereby making the knocking sound once the elastic element passes over a sliding surface of the non-elastic element during rotation to close the lid, the sliding surface being substantially parallel to the outer surface of the lid,
   wherein the knocking sound indicates formation of a liquid tight seal of the opening and the start of a detection assay by the detecting element when in use, and wherein a detection result is displayed on the detecting element after an allotted time starting from the generation of the sound,
   wherein the elastic element and the non-elastic element each have sloped surfaces that are perpendicular to the outer surface of the lid and that oppose and engage each other when the lid is rotated to open the detecting chamber, the sloped surfaces operably configured to elastically deform the elastic element in a direction perpendicular to the direction of lid rotation, and
   wherein the rotation of the lid to open the detecting chamber urges the non-elastic element to pass over the top surface of the elastic element thereby allowing removal of the lid.
2. The device of claim 1, wherein the lid edge comprises a first elongated gap traversing a width of the lid edge located adjacent the non-elastic element disposed on the outer surface of the lid edge.

3. The device of claim 2, wherein the lid edge comprises a second elongated gap traversing a width of the lid edge located adjacent the non-elastic element disposed on the outer surface of the lid edge.

4. The device of claim 3, wherein the first elongated gap extends substantially parallel to a length of the sliding surface of the non-elastic element.

5. The device of claim 4, wherein the second elongated gap extends substantially perpendicular to a length of the sliding surface of the non-elastic element.

6. The device of claim 1, wherein the elastic element disposed on the collecting chamber is moved radially away from the lid edge when moved along the sliding surface of the non-elastic element disposed on the lid edge.

7. The device of claim 1, wherein the detecting chamber is disposed in a sidewall of the collecting chamber.

8. The device of claim 1, wherein the elastic element disposed on the collecting chamber is configured to prevent removal of the lid from the collecting chamber once the sound is generated.

9. The device of claim 1, wherein the indicating device consists of a single elastic element disposed on the collecting chamber and a single non-elastic element disposed on the lid edge.

10. A method for detecting an analyte in a sample, comprising:
 a) adding a sample to the collecting chamber of the device of claim 1; and
 b) closing the opening of the collecting chamber by moving the lid to the appointed position, thereby generating a sound, sealing the opening and initiating a detection assay.

11. The method of claim 10, further comprising analyzing results of the detecting assay after a predetermined amount of time from when the sound is generated.

12. The method of claim 10, wherein the sample is a bodily fluid.

13. The method of claim 12, wherein the sample is urine or saliva.

* * * * *